United States Patent
Suh (10) Patent No.: US 6,471,679 B1
(45) Date of Patent: Oct. 29, 2002

(54) PORTABLE NASAL MUCUS REMOVING DEVICE

(75) Inventor: Jeong-Joo Suh, Seoul (KR)

(73) Assignee: G-Intek Co., Ltd., Seoul (KR)

( * ) Notice: Subject to any disclaimer, the term of this patent is extended or adjusted under 35 U.S.C. 154(b) by 90 days.

(21) Appl. No.: 09/607,187

(22) Filed: Jun. 29, 2000

(30) Foreign Application Priority Data

Feb. 8, 2000 (KR) .......................................... 2000-5826

(51) Int. Cl.$^7$ ............................................... A61M 1/00
(52) U.S. Cl. ...................................... 604/319; 604/904
(58) Field of Search ................................ 604/318–326, 604/73–74, 902; 606/162

(56) References Cited

U.S. PATENT DOCUMENTS

| 4,929,229 A | * | 5/1990 | Larsson | ........................ | 604/74 |
| 6,045,529 A | * | 4/2000 | Nuesch | ........................ | 604/74 |
| 6,139,521 A | * | 10/2000 | Larsson | ........................ | 604/74 |

* cited by examiner

Primary Examiner—Glenn K. Dawson
Assistant Examiner—C. Lynne Anderson
(74) Attorney, Agent, or Firm—Christie, Parker & Hale, LLP (57) ABSTRACT

A portable nasal, mucus removing device includes a case having an internal empty space for receiving parts, and a motor placed within the case and rotated by receipt of driving power from a battery. A power transmission unit is connected to the motor to convert the rotating movement of the motor into a reciprocating movement. A vacuum generator is connected to the power transmission unit to generate a vacuum pressure by introducing an external air or discharging the introduced air. A storage tank is connected to the case from the outside such that the storage tank can be separated from the case. The storage tank air-communicates with the vacuum generator via an air-introducing tube. An entrance tube is externally combined with the storage tank to introduce a nasal mucus. A guide tube is attached to an inner wall of the storage tank to guide the introduced nasal mucus into the storage tank. A control unit for controlling the vacuum pressure in the vacuum generator is provided at the case to induce or stop the introduction of the nasal mucus.

21 Claims, 8 Drawing Sheets

PORTABLE NASAL MUCUS REMOVING DEVICE

BACKGROUND OF THE INVENTION (a) Field of the Invention

The present invention relates to a portable nasal mucus removing device and, more particularly, to a portable nasal mucus removing device which can perform the nasal mucus removing operation in an efficient manner with a compact structure.

(b) Description of the Related Art

Generally, infants bearing weakness to various kinds of things easily catch virus-induced diseases at respiratory organs. When such diseases are caught, a clear slimy liquid, formally called the "nasal mucus", is produced from the inside of the nose so that the nose is blocked with the mucus. This is liable to induce difficulty in breathing and, consequently, make serious damages to the body. The situation is the same in adults due to a cold, an allergy-induced nasitis, or an ozena.

In order to remove the nasal mucus from the nose, toilet papers or cotton bars are frequently used. However, in this case, the skin of the nose or the skin surrounding the nose is rubbed due to the friction of the toilet papers or the cotton bars so that skin damages are resulted with the leftover nasal mucus.

Recently, nasal mucus removing devices using electric motor have been extensively used. The nasal mucus removing devices are usually classified into a pump type and an impeller type. The pump typed removing device can exert relatively high attraction power for removing the nasal mucus from the nose, but involves several problems. That is, in such a device, a piston reciprocates within the cylinder while contacting the inner wall of the cylinder so that high energy is consumed, and working efficiency is deteriorated. Furthermore, in the course of generating a vacuum atmosphere, the reciprocating movement of the piston induces serious vibration, resulting in device failure.

The impeller typed removing device exhibits lower consumption energy, but does not produce high attraction power due to the whirlpool of fans.

Furthermore, such kinds of nasal mucus removing devices take a relatively large volume, and involve inconvenience in use and carriage.

SUMMARY OF THE INVENTION

It is an object of the present invention to provide a portable nasal mucus removing device which keeps a high-pressure attraction power for introducing the nasal mucus in a constant manner to completely remove the nasal mucus from the nose, and has a compact structure capable of giving the user great convenience in use and carriage.

This and other objects may be achieved by a portable nasal mucus removing device including a case having an internal empty space for receiving parts. A motor is placed within the case, and rotated by receipt of driving power from a battery. A power transmission unit is connected to the motor to convert the rotating movement of the motor into a reciprocating movement. A vacuum generator is connected to the power transmission unit to generate a vacuum pressure by introducing an external air or discharging the introduced air. A storage tank is connected to the case from the outside such that the storage tank can be separated from the case. The storage tank air-communicates with the vacuum generator via an air-introducing member. An entrance tube is externally combined with the storage tank to introduce a nasal mucus. A guide tube is attached to an inner wall of the storage tank to guide the introduced nasal mucus into the storage tank. A control unit for controlling the vacuum pressure in the vacuum generator is provided at the case to induce or stop the introduction of the nasal mucus.

A flywheel is provided at the power transmission unit to help the rotating shaft to rotate at a regular speed and enhance the rotating energy of the rotating shaft by its own weight. A plurality of ribs is provided between the inner wall of the case and the motor to make the insertion of the motor into the case in a tight manner, and disperse and absorb vibration or shaking of the motor.

A valve is provided at the vacuum generator to control the vacuum pressure for introducing an external air or discharging the introduced air. The central portion of the valve moves up and downwards while its peripheral portion being fixed. The valve has no friction factors so that energy consumption is minimized with the effect of high energy efficiency.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or the similar components, wherein.

DETAILED DESCRIPTION OF THE PREFERRED EMBODIMENTS

Preferred embodiments of this invention will be explained with reference to the accompanying drawings.

Figure 1:
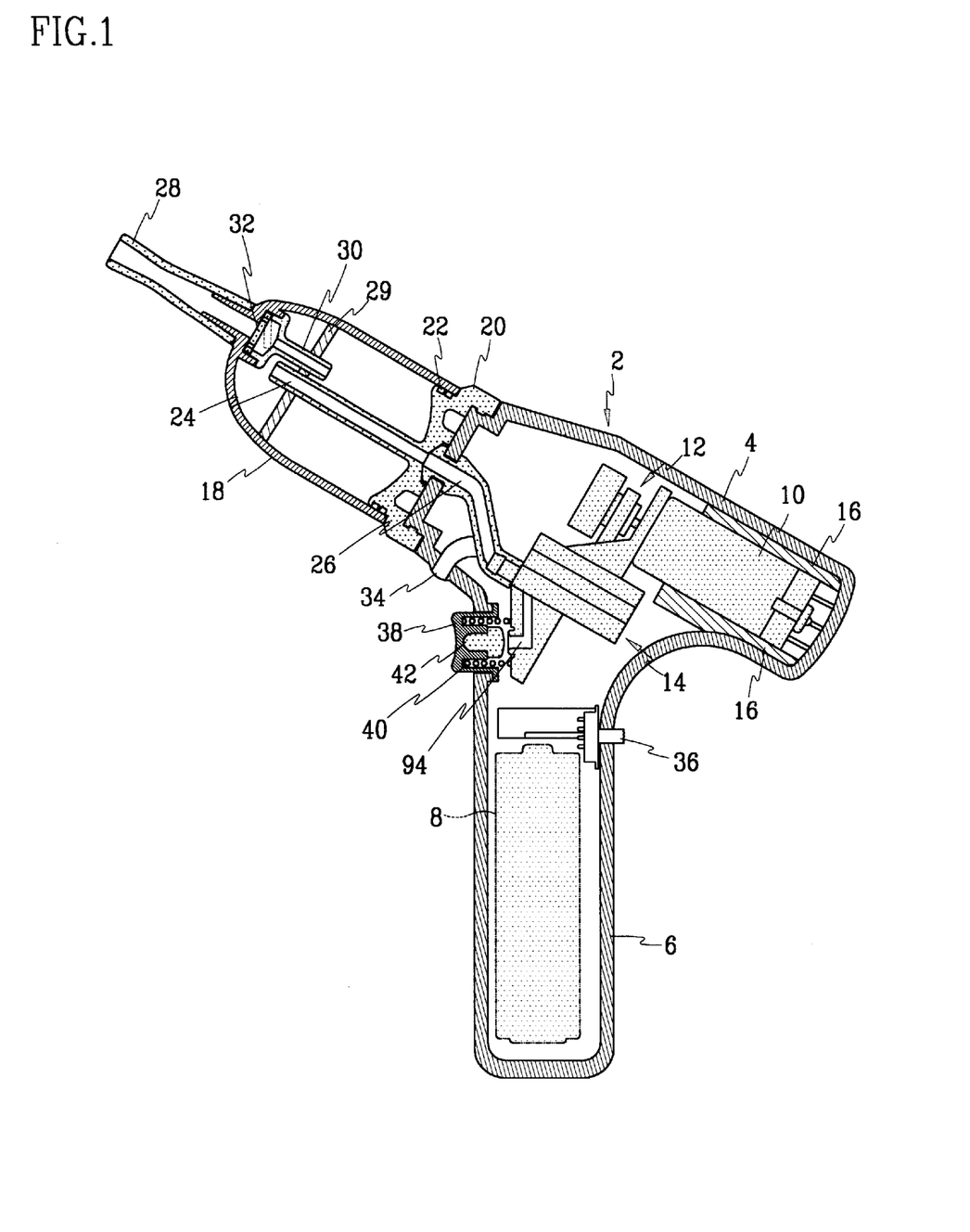
FIG. 1 is a side cross-sectional view of a portable nasal mucus removing device with a valve seat, and an air in-outputting member according to a preferred embodiment of the present invention.
Figure 2:
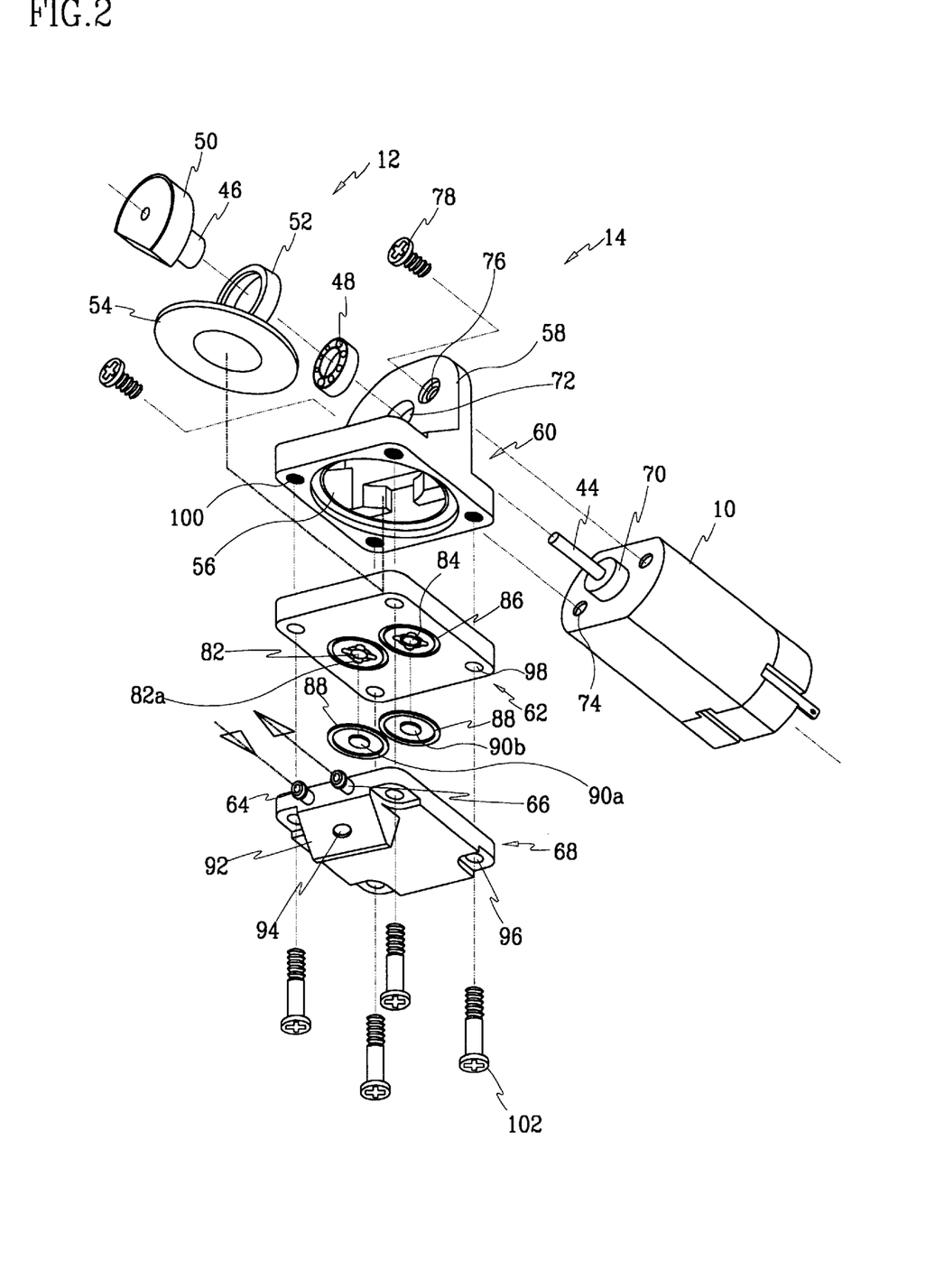
FIG. 2 is an exploded perspective view of the portable nasal mucus removing device shown in FIG. 1.

FIG. 1 is a side cross-sectional view of a nasal mucus removing device according to a preferred embodiment of the present invention, FIG. 2 is an exploded perspective view of the nasal mucus removing device. In the drawings, the reference numeral 2 indicates a case.

The case 2 is formed with a main body 4 for receiving various kinds of parts, and a handle 6 extended from the body 4 downwards. A battery 8 is positioned within the handle 6 of the case 2.

The body 4 of the case 2 is provided with a motor 10 electrically connected to the battery 8 at its rear portion, a power transmission unit 12 linearly connected to the motor 10 to convert the rotating movement of the motor 10 into a reciprocating movement, and a vacuum generator 14 connected to the bottom side of the power transmission unit 12. When the power transmission unit 12 is operated, the vacuum generator 14 discharges an internal air to the outside to produce the required vacuum pressure therein.

A plurality of ribs 16 are formed to be integrated with the inner wall of the main body 4 such that they can disperse or absorb vibration or shaking of the motor 10 due to the rotating movement.

A storage tank 18 for storing the nasal mucus is connected to the frontal side of the main body 4 of the case 2 via a lid 20. The lid 20 is combined with the storage tank 18 such that it can be separated from the latter. The lid 20 can be also separated from the case 2.

A packing 22 is provided between the storage tank 18 and the lid 20 to prevent outflow of the nasal mucus from the storage tank 18 and to keep the storage tank 18 secret.

An air-introducing tube 24 is linearly extended from the lid 20 toward the inside of the storage tank 18. The air introducing tube 24 tightly contacts a ventilation tube 26 connected to the vacuum generator 14 face by face while communicating with the ventilation tube 26.

An entrance tube 28 for introducing the nasal mucus is connected to the storage tank 18 opposite to the lid 20 such that it can be separated from the storage tank 18. A guide tube 30 for guiding the flow of the introduced nasal mucus is attached to the inner wall of the storage tank 10 such that it can communicate with the entrance tube 28.

A blocking member 29 is fixed to the inner wall of the storage tank 18 to prevent passage of the contents of the nasal mucus having viscosity while allowing passage of the water content.

The free end portion of the air-introducing tube 24 is displaced with that of the guide tube 30 while proceeding opposite to each other such that the nasal mucus contained in the storage tank 18 does not intrude into the air-introducing tube 24. For this purpose, the blocking member 29 is also positioned between the free end portions of the guide tube 30 and the air-introducing tube 24.

Considering that the entrance tube 28 should be inserted into the nose to remove the nasal mucus therein, it is preferably formed with flexible materials such as a silicon rubber.

A reverse-flow blocking valve 32 is provided in-between the entrance tube 28 and the guide tube 30 to prevent outflow of the nasal mucus from the storage tank 18 toward the entrance tube 28.

The reverse-flow blocking valve 32 may be formed with flexible materials such as a rubber. The reverse-flow blocking valve 32 is usually in a closing state, but in operation, the lower portion thereof opens as indicated by a dotted line of FIG. 1.

An air exhaust tube 34 is provided at the bottom side of the main body 4 of the case 2 to exhaust the air introduced into the vacuum generator 2 through the air-introducing tube 24 and the ventilation tube 26 to the outside.

A switch 36 is provided at the handle 6 of the case 2 to operate the motor 10. A control unit is further provided at the handle 6 to control the inner pressure of the vacuum generator 14.

The control unit includes a button 38 attached to the handle 6 such that it can be pushed from the outside, an elastic member 40 tensioned between the button 38 and the vacuum generator 14, and a vacuum pressure control member 42 connected to the rear of the button 38 to control the inner pressure of the vacuum generator 14.

The vacuum pressure control member 42 is preferably formed with elastic materials such as a silicon or a rubber.

As shown in FIG. 2, the power transmission unit 12 includes an eccentric cam 46 inserted onto a rotating shaft 44 of the motor 10, a bearing 48 inserted onto the eccentric cam 46 to reduce the rotational resistance of the motor 10 and support the rotating shaft 44, a flywheel 50 connected to the eccentric cam 46 in a body and inserted onto the rotating shaft 44, and a power transmission member 52 inserted onto the bearing 48 to convert the rotating movement of the eccentric cam 46 into the reciprocating movement. The flywheel 50 is to help the rotating shaft 44 to rotate at a regular speed and enhance the rotating energy of the rotating shaft 44 by its own weight.

Alternatively, the flywheel 50 may be made separately from the eccentric cam 46, and combined with the rotating shaft 44.

The power transmission member 52 is structured such that one side thereof crosses the rotating shaft 44 of the motor 10, and the opposite side is connected to the vacuum generator 14.

The vacuum generator 14 includes a flying saucer-shaped valve 54 connected to the power transmission member 52, a fixation member 60 having a central opening portion 56 for receiving the top portion of the flying saucer shaped valve 54 and a fixation plate 58, a valve seat 62 combined with the fixation member 60 by interposing the flying saucer-shaped valve 54, and an air in-outputting member 68 positioned under the valve seat 62. The air in-outputting member 68 has an inlet and outlet tubes 64 and 66 for introducing or discharging air according to the operation of the flying saucer-shaped valve 54.

The flying saucer-shaped valve 54 is preferably formed with elastic materials such as a rubber. The peripheral portion of the flying saucer-shaped valve 54 is established to be thinner than its central portion such that the up and down movements thereof can be fluently performed. Accordingly, when the flying saucer-shaped valve 54 moves up and downwards, friction factors are not present so that the energy consumption is reduced with the effect of high energy efficiency.

The fixation plate 58 of the fixation member 60 is provided with an opening portion 72 for receiving and supporting a shaft support 70 surrounding the rotating shaft 44 of the motor 10, and a plurality of combination holes 76 corresponding to screwed opening portions 74 formed at the motor 10. Fixtures 78 such as a screw or bolt is inserted into the screwed opening portion 74 of the motor 10 through the combination holes 76 of the fixation plate 76.

The valve seat 62 have an upper region with a central hollowed portion for forming a vacuum space 80, and a lower region with an inlet port 82 and an outlet port 84 communicating with the vacuum space 80.

Figure 3:
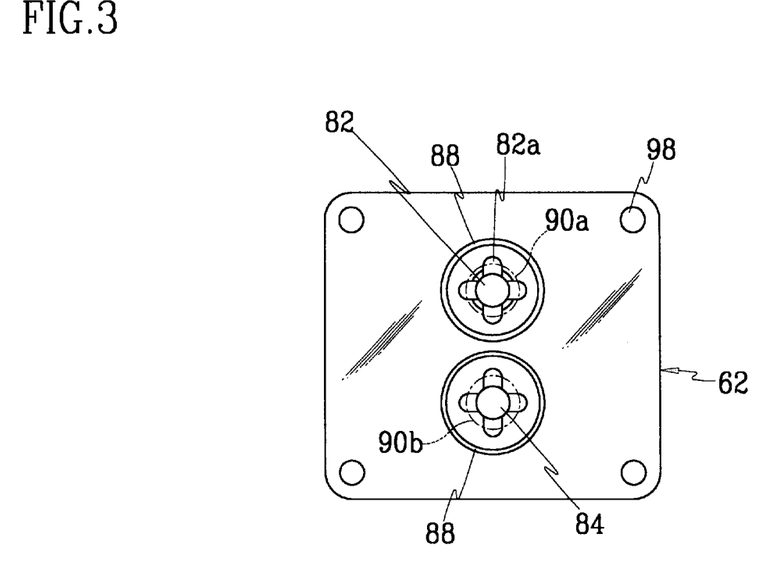
FIG. 3 is a bottom plan view of the valve seat of the portable nasal mucus removing device shown in FIG. 1.
Figure 4:
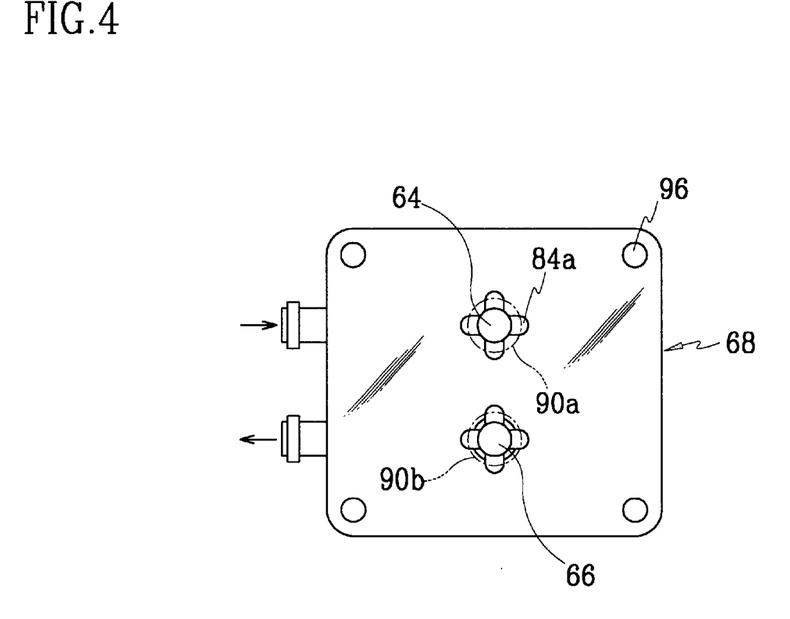
FIG. 4 is a plan view of the air in-outputting member of the portable nasal mucus removing device shown in FIG. 1.

The inlet and outlet ports 82 and 84 are positioned above the bottom surface of the valve seat 62. As shown in FIG. 3, the valve seat 62 is further provided with a plurality of subsidiary inlet ports 82a externally surrounding the inlet port 82 in a radial manner. As shown in FIG. 4, the air in-outputting member 68 positioned under the valve seat 62 is provided with a plurality of subsidiary outlet ports 84a formed at the outlet tube 66 while externally surrounding the bottom side of the outlet port 84 of the valve seat 62 in a radial manner.

A circular-shaped groove 86 externally surrounds each of the inlet and outlet ports 82 and 84. An O-shaped ring 88 is inserted into the groove 86 to keep secret between the valve seat 62 and the air in-outputting member 68. First and second switching plates 90a and 90b capable of covering the inlet and outlet ports 82 and 84 but not the subsidiary inlet and outlet ports 82a and 84a are provided at the inlet and outlet ports 82 and 84, respectively.

The first and second switching plate 90a and 90b is preferably formed with elastic materials such as a rubber or a silicon such that they can completely block the outlet tube 66 and the outlet port 84 when needed.

When the flying saucer-shaped valve 54 moves upwards at its central portion while being fixed between the fixation member 60 and the valve seat 62 at its peripheral portion, the first and second switching plates 90a and 90b are elevated due to air pressure working at the vacuum space 80. Since the subsidiary inlet ports 82a positioned to be external to the first switching plate 90a are not closed while the outlet port 84 being closed by the second switching plate 90b, an external air is introduced into the vacuum space 80 through the subsidiary inlet ports 82a and the inlet port 82.

In contrast, when the flying saucer-shaped valve 54 moves downwards, the first and second switching plate 90a and 90b are lowered. At this time, the first switching plate 90a closes the inlet tube 64, whereas the second switching plate 90b only partially closes the outlet tube 66 because it does not cover the subsidiary outlet ports 84a. Therefore, the air contained in the vacuum space 80 of the valve seat 62 is discharged to the outside through the subsidiary outlet ports 84a and the outlet tube 66.

The inlet tube 64 of the air in-outputting member 68 communicates with the ventilation tube 26 connected to the air-introducing tube 24, whereas the outlet tube 66 communicates with the air exhaust tube 34.

A protrusion 92 with an extension tube 94 is extended from the bottom side of the air in-outputting member 68. The extension tube 94 communicates with the inlet tube 64.

The extension tube 94 is structured to open or close according to the operation of the button 38 to thereby make a vacuum atmosphere in the vacuum generator 14 or dissipate it.

That is, even when the motor 10 is rotated to thereby operate the flying saucer-shaped valve 54, the extension tube 94 is in an opening state due to the elasticity of the elastic member 40 tensioned between the extension 92 and the button 38. An external air is introduced into the vacuum generator 14 through the extension tube 94 and the inlet tube 64, and the introduced air is discharged to the outside through the outlet tube 66. In this state, since the amount of the introduced air is larger than that of the discharged air, the vacuum pressure in the vacuum generator 14 is lower so that practical attraction power for introducing the nasal mucus is not generated.

When the user pushes the button 38, the vacuum pressure control member 42 overcomes the elasticity of the elastic member 40 to thereby close the extension tube 94 so that appropriate vacuum pressure is made at the vacuum generator 14 and exerts the required attraction power.

A plurality of holes 96 and 98 are formed at the valve seat 62 and the air in-outputting member 68 such that the neighboring holes 96 and 98 are positioned on the same axis. In the same way, screwed opening portions 100 are formed at the fixation member 60. The holes 96 and 98 of the valve seat 62 and the air in-outputting member 68 agree to the corresponding screwed opening portion 100 of the fixation member 60, and fixtures 102 such as a screw or a bolt are inserted into the holes 96 and 98, and fixed within the screwed opening portions 100.

When the above-described portable nasal mucus removing device is practically used, the switch 36 is first made to be in an on state, and the entrance tube 28 is inserted into the nose.

The motor 10 is driven upon receipt of driving power from the battery 8, and the eccentric cam 46 connected to the rotating shaft 44 of the motor 10 is rotated. The power transmission member 52 inserted onto the eccentric cam 46 via the bearing 48 transmits the rotating power of the eccentric cam 46 to the flying saucer-shaped valve 54 while converting the rotating movement into a reciprocating movement.

The center portion of the flying saucer-shaped valve 54 reciprocates up and downwards while its peripheral portion being fixed between the fixation member 60 and the valve seat 62.

At this time, air is introduced into the vacuum generator 14 through the inlet tube 64 and the extension tube 94. The air introduced into the vacuum generator 14 is discharged through the outlet tube 66 so that the vacuum degree of the vacuum generator 14 is not so high as to exert suitable attraction power.

FIGS. 5A to 6C illustrate the vacuum pressure controlling process of the nasal mucus removing device shown in FIG. 1 in detail.

Figure 5A:
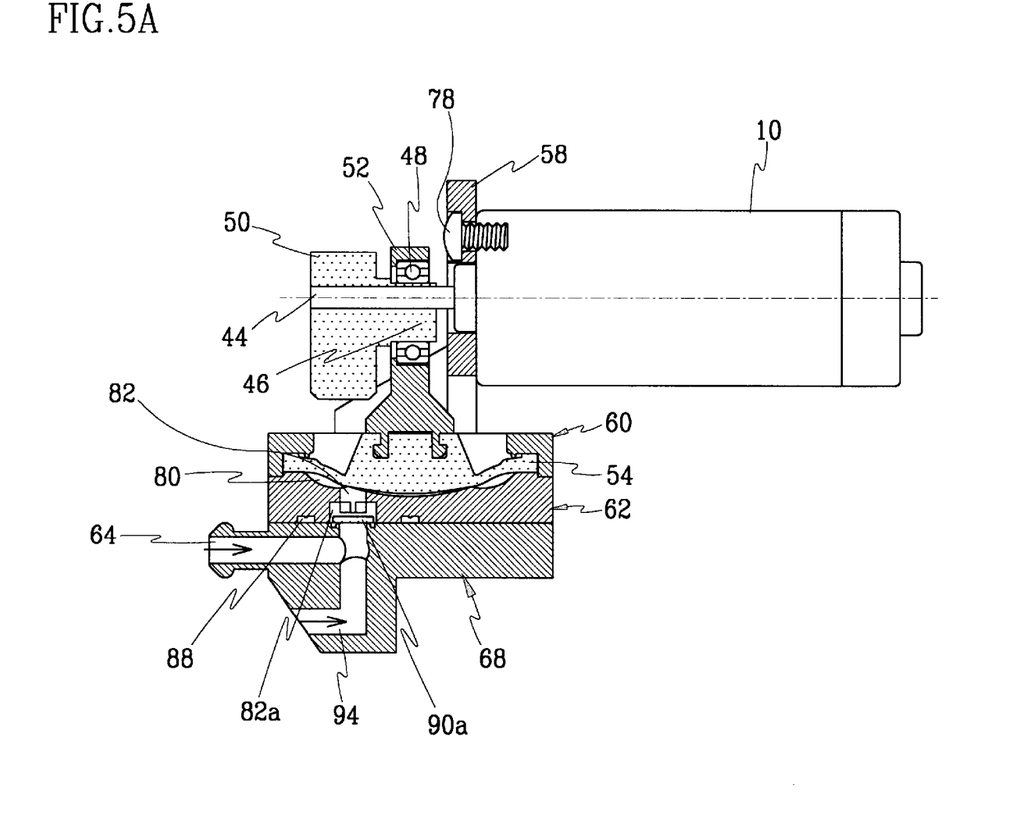
FIGS. 5A to 5F are side elevation views illustrating the vacuum pressure controlling process of the portable nasal mucus removing device shown in FIG. 1.
Figure 5B:
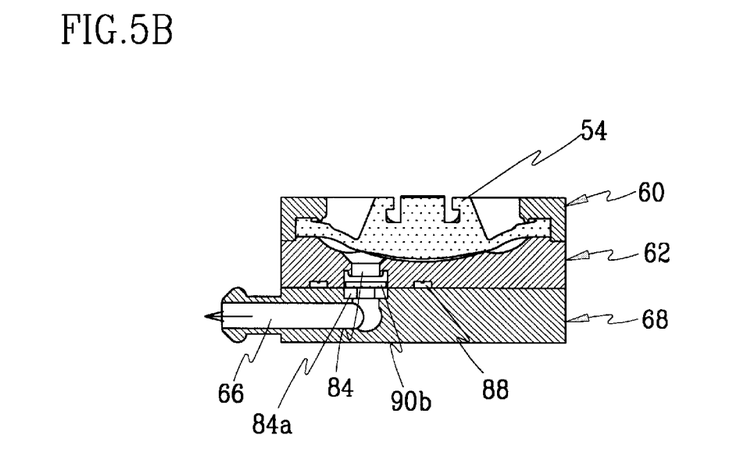
Figure 6A:
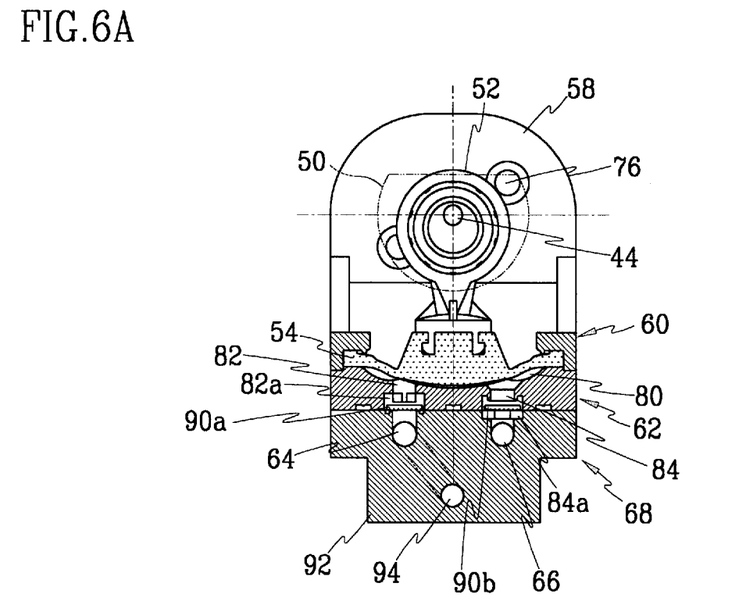
FIGS. 6A to 6C are front elevation views illustrating the vacuum pressure controlling process of the portable nasal mucus removing device shown in FIG. 1.

As shown in FIGS. 5A, 5B and 6A, when the power transmission member 52 moves downwards, the flying saucer-shaped valve 54 is lowered, and contacts the bottom side of the hollowed portion of the valve seat so that the first and second switching plates 90a and 90b closes the inlet tube 64 and the outlet tube 66, respectively.

Figure 5C:
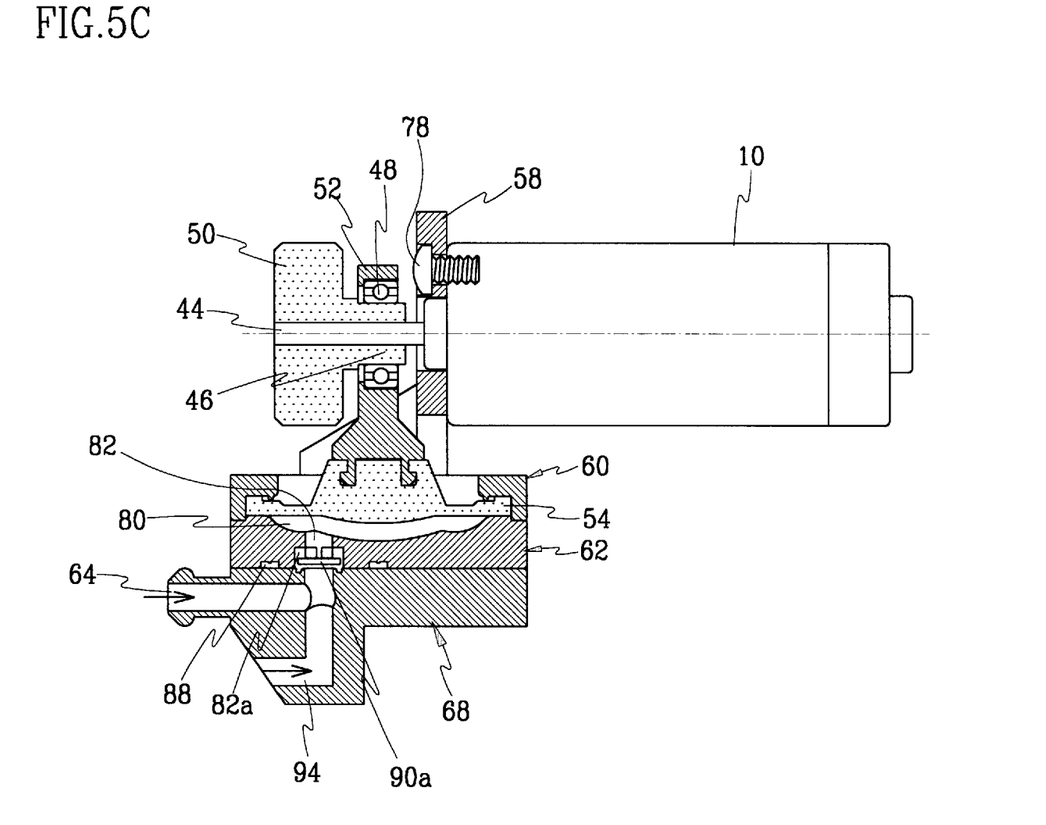
Figure 5D:
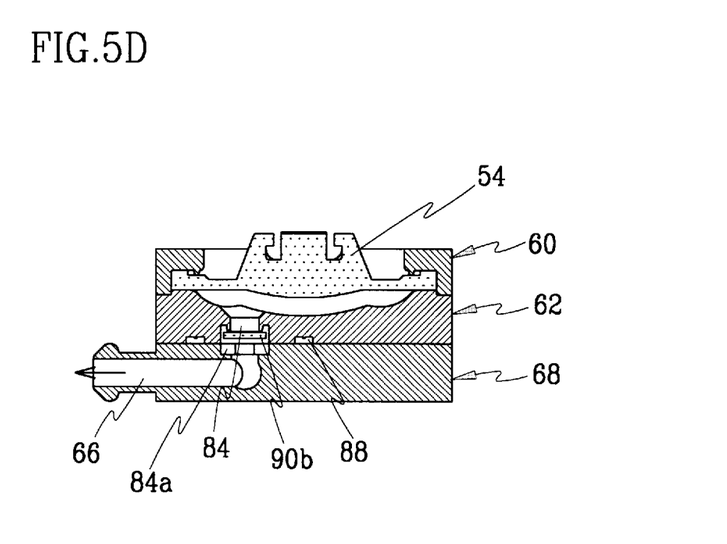
Figure 5E:
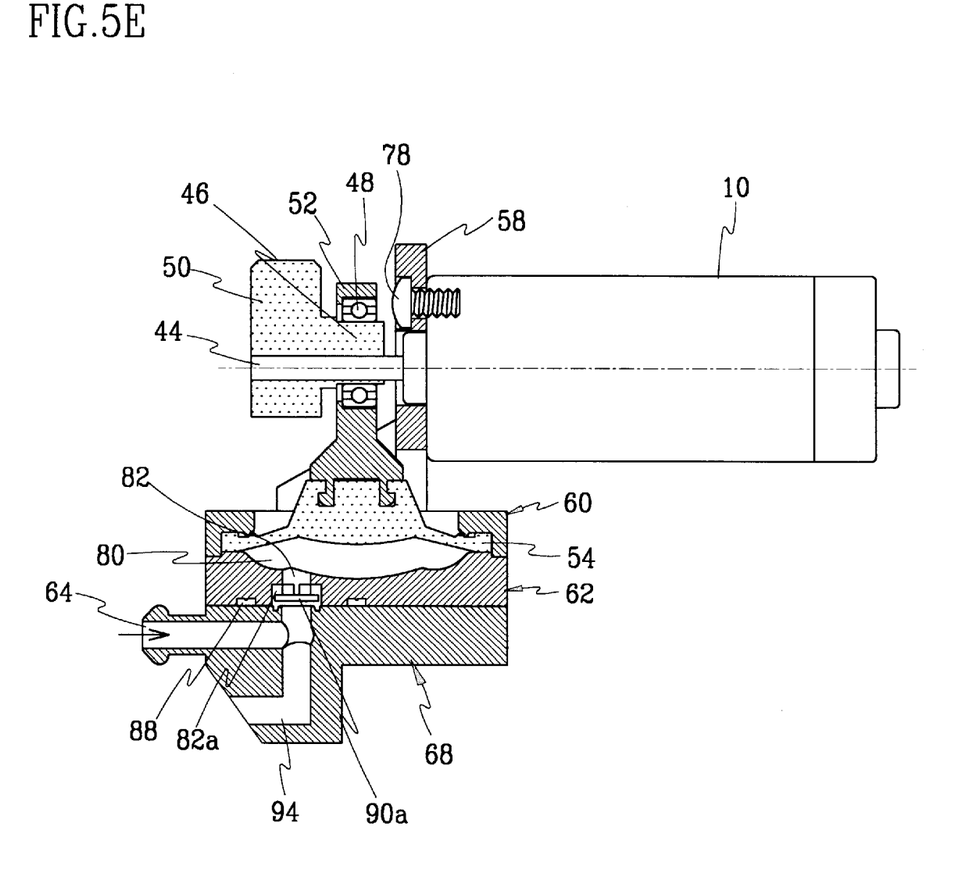
Figure 5F:
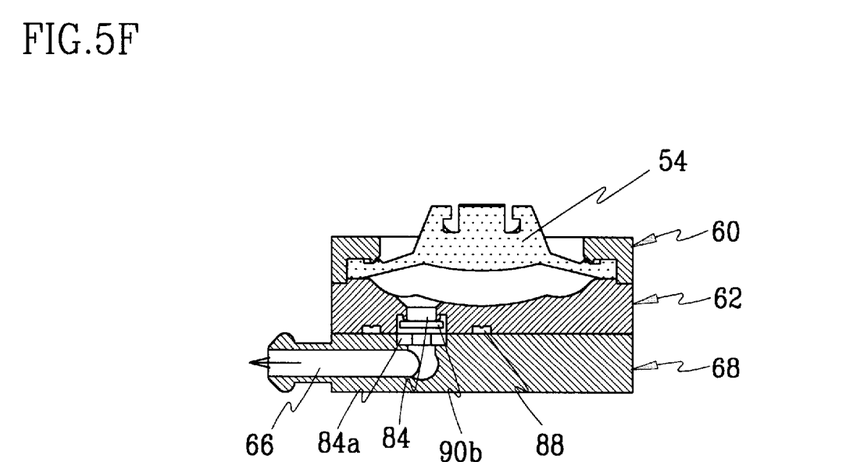
Figure 6B:
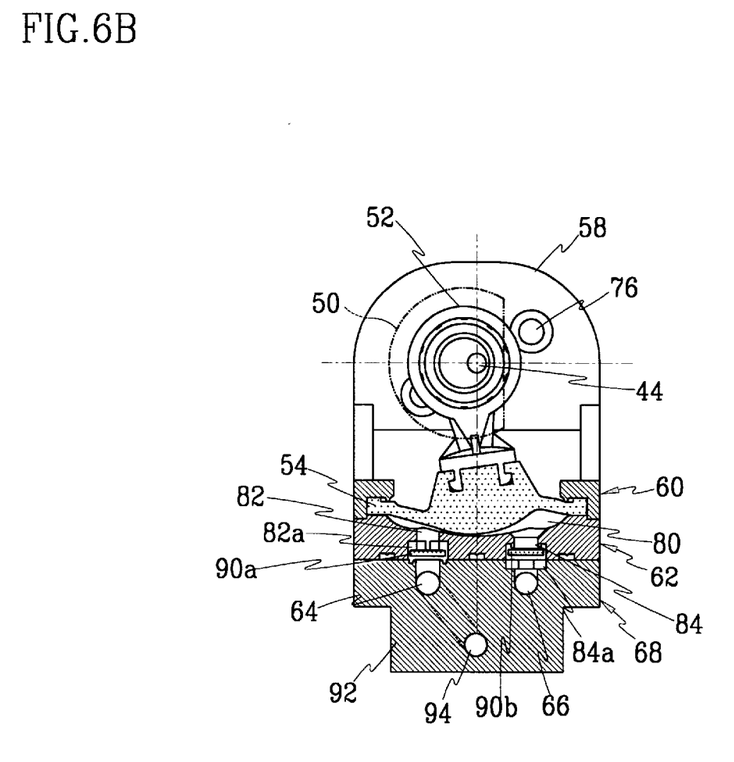
Figure 6C:
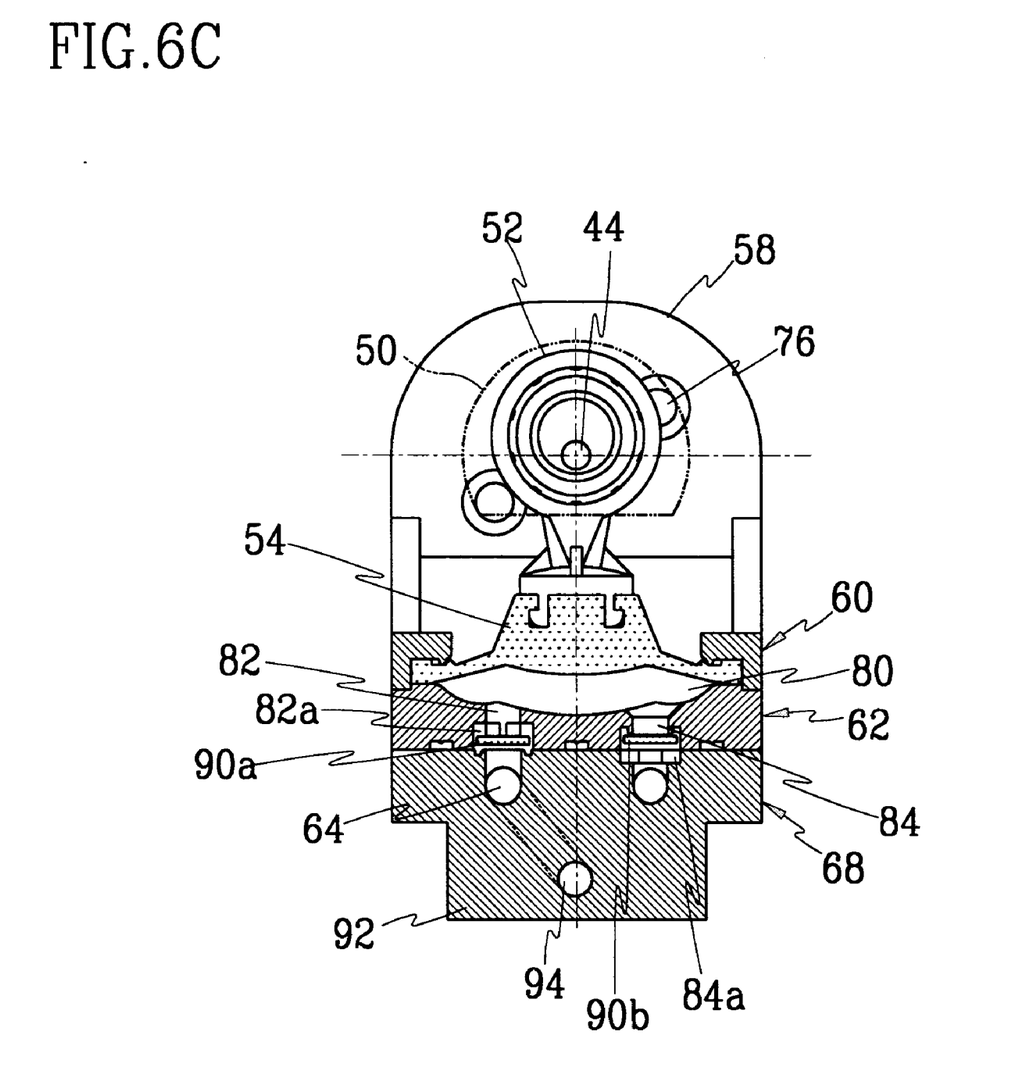

As shown in FIGS. 5C, 5D and 6B, when the motor 10 is rotated, the eccentric cam 46 combined with the rotating shaft 44 is rotated, and hence the power transmission member 52 moves upwards. At this time, the center portion of the flying saucer-shaped valve 54 combined with the power transmission member 52 is elevated together with the first and second switching plate 90a and 90b.

The second switching plate 90b closes the outlet port 84, and the first switching plate 90a closes the bottom side of the inlet port 82. Since the inlet port 82 communicates with the subsidiary inlet ports 82a, an air is introduced into the vacuum space 80 of the vacuum generator 14 through the subsidiary inlet ports 82a and the inlet port 82.

In this operation, due to the eccentric rotation of the eccentric cam 46, the overall portions of the flying saucer-shaped valve 54 is not uniformly elevated such that one sided portion of the flying saucer-shaped valve 54 first moves upwards. In such an operating structure, the air contained in the vacuum space 80 of the vacuum generator 14 is completely discharged, and then an external air is newly introduced into the vacuum space 80. This makes it possible to introduce larger amount of air into the vacuum space 80.

When the motor 10 is further rotated such that the power transmission member 52 reaches its uppermost position, still larger amount of air is introduced into the vacuum space 80.

As shown in FIGS. 5A, 5B and 6A, when the motor 10 is still further rotated, the power transmission member 52 moves downwards so that the first and second switching plates 90a and 90b are pushed toward the air in-outputting member 68. As a result, the first switching plate 90a closes the inlet tube 64. Since the subsidiary outlet ports 84a communicate with the outlet tube 66, the air contained in the hollowed portion 80 is discharged to the outside through the outlet port 84, subsidiary outlet ports 84a and the outlet tube 66.

When the above procedures are repeated in a short time and the button 38 of the control unit attached to the handle 6 of the case 2 is pushed, the button 38 overcomes the elasticity of the elastic member 40, and the vacuum pressure control member 42 closes the extension tube 94 formed at the air in-outputting member 68.

Then, the nasal mucus is introduced through the entrance tube 28 and the guide tube 30, and stored in the storage tank 18 between the blocking member 29 and the lid 20.

Since the free end portions of the guide tube 30 and the air-introducing tube 24 proceed in the opposite directions, and the nasal mucus is blocked by the blocking member 29, the introduced nasal mucus does not flow into the vacuum generator 14.

The air introduced into the storage tank together with the nasal mucus is flowed into the vacuum generator 14 through the air-introducing tube 24, the ventilation tube 26 and the inlet tube 64, and discharged to the outside through the outlet tube 66 and the air exhaust tube 34.

When the user releases the button 38 to temporarily stop the inflow of the nasal mucus, the vacuum pressure control member 42 moves back from the extension tube 94 due to the elasticity of the elastic member 40 so that an external air is introduced into the vacuum generator 14 through the extension tube 94, and the vacuum pressure of the vacuum generator 14 is dissipated.

When the switch 36 is off, the rotation of the motor 10 stops so that the operation of the nasal mucus removing device is terminated.

If the storage tank 18 is filled with a predetermined quantity of nasal mucus, the storage tank 18 is separated from the case 2 together with the lid 20. The lid 20 is detached from the storage tank 18, and the nasal mucus contained in the storage tank 18 is discarded at an appropriate place. Thereafter, the blocking member 29 and the storage tank 18 are cleaned, and the lid 20 is attached to the storage tank 18. The lid 20 attached to the storage tank 18 is then combined with the case 2 for reuse.

As described above, in the inventive nasal mucus removing device, the vacuum generator and the power transmission member with the flywheel make it possible to completely remove the nasal mucus from the nose.

Furthermore, the flying saucer-shaped valve serves to make appropriate vacuum pressure within the vacuum generator in such a state that its peripheral portion is fixed and only its center portion moves up and downwards. Consequently, friction factors are not present so that energy consumption is reduced with the effect of high energy efficiency.

In addition, the vibration of the motor is prevented, and the overall device has a compact structure so that the user can use and carry it in a convenient manner.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A portable nasal mucus removing device:

a case having an internal empty space for receiving parts;

a motor placed within the case and rotated by receipt of driving power from a battery;

a power transmission unit connected to the motor to convert the rotating movement of the motor into a reciprocating movement, wherein the power transmission unit comprises an eccentric cam fixed to a rotating shaft of the motor, a bearing surrounding the eccentric cam to minimize the rotational resistance of the motor and support the rotating shaft, and a power transmission member connected to the bearing to convert the rotating movement of the motor into a reciprocating movement;

a vacuum generator connected to the power transmission unit to generate a vacuum pressure by introducing an external air or discharging the introduced air, wherein the vacuum generator comprises a valve connected to the power transmission member, a fixation member having a central opening portion for receiving the valve and a fixation plate, a valve seat positioned under the fixation member, and an air in-outputting member positioned under the valve seat to control the introduction and discharging of the air together with the valve seat by the operation of the valve, and wherein the valve is formed with an elastic rubber, the peripheral portion of the valve being thinner than the central portion of the valve to fluently perform a reciprocating movement;

a storage tank connected to the case from the outside such that the storage tank can be separated from the case, the storage tank air-communicating with the vacuum generator via an air-introducing tube;

an entrance tube externally combined with the storage tank to introduce a nasal mucus;

a guide tube attached to an inner wall of the storage tank to guide the introduced nasal mucus into the storage tank; and a control unit for controlling the vacuum pressure in the vacuum generator to induce or stop the introduction of the nasal mucus.

2. The nasal mucus removing device of claim 1 further comprising a flywheel for helping the rotating shaft to rotate at a regular speed and enhancing the rotating energy of the rotating shaft by the self weight.

3. The nasal mucus removing device of claim 3 wherein the flywheel is connected to the eccentric cam in a body, or made separately from the eccentric cam.

4. The nasal mucus removing device of claim 1 further comprising a plurality of ribs for making the insertion of the motor into the case in a tight manner, and dispersing and absorbing vibration or shaking of the motor.

5. The portable nasal mucus removing device of claim 1 wherein the valve comprises a central portion and a peripheral portion, the peripheral portion of the valve being fixed between the fixation member and the valve seat, the central portion of the valve being reciprocating to generate an appropriate vacuum pressure, the valve having no friction factors to effect high energy efficiency.

6. The portable nasal mucus removing device of claim 1 wherein the valve seat comprises a hollowed portion for forming a vacuum space, inlet and outlet ports communicating with the vacuum space to introduce an air and discharge the introduced air, a plurality of subsidiary inlet ports radially surrounding the bottom side of the inlet port, and first and second switching plates selectively opening and closing the inlet and outlet ports according to the reciprocating movement of the valve.

7. The portable nasal mucus removing device of claim 6 wherein a circular groove surrounds the inlet and outlet ports, and an O-shaped ring is inserted into the groove to make the valve seat secret.

8. The portable nasal mucus removing device of claim 6 wherein the air in-outputting member comprises an inlet tube communicating with the inlet port to introduce an external air, an outlet tube communicating with the outlet port to discharge the introduced air to the outside, and a plurality of subsidiary outlet ports formed at the outlet tube while radially surrounding the bottom side of the outlet port.

9. The portable nasal mucus removing device of claim 1 wherein a protrusion is extended from the bottom side of the air in-outputting member, and the protrusion is provided with an extension tube for controlling the vacuum pressure in the vacuum generator.

10. The portable nasal mucus removing device of claim 6 wherein the first and second switching plates has a size capable of covering the inlet and outlet ports of the valve seat, but not the subsidiary inlet and outlet ports surrounding the inlet and outlet ports such that the first and second switching plates move upwards while opening the subsidiary inlet ports communicating with the inlet port and closing the outlet port to thereby introduce an external air, and the first and second switching plates move downwards while closing the inlet port and closing the outlet port communicating with the subsidiary outlet ports to thereby discharge the introduced air.

11. The portable nasal mucus removing device of claim 1 wherein the entrance tube comprises free end portions and wherein the free end portions of the entrance tube and the air-introducing tube are displaced at different planes.

12. The portable nasal mucus removing device of claim 1 wherein a blocking member is provided within the storage tank to prevent passage of the contents of the nasal mucus having viscosity but allow passage of a water content.

13. The portable nasal mucus removing device of claim 1 wherein a reverse-flow blocking valve is provided at the storage tank to prevent outflow of the nasal mucus contained in the storage tank.

14. The portable nasal mucus removing device of claim 13 wherein the reverse-flow blocking valve is formed with elastic materials such as a rubber, the reverse-flow blocking valve opening only when the nasal mucus is introduced.

15. The portable nasal mucus removing device of claim 1 wherein the control unit comprises a button attached to the case such that the button can be pushed from the outside, an elastic member tensioned between the button and the vacuum generator, and a vacuum pressure control member connected to the rear of the button to open or close an extension tube of the vacuum generator.

16. A portable nasal mucus removing device:
a case having an internal empty space for receiving parts;
a motor placed within the case and rotated by receipt of driving power from a battery;
a power transmission unit connected to the motor to convert the rotating movement of the motor into a reciprocating movement, wherein the power transmission unit comprises an eccentric cam fixed to a rotating shaft of the motor, a bearing surrounding the eccentric cam to minimize the rotational resistance of the motor and support the rotating shaft, and a power transmission member connected to the bearing to convert the rotating movement of the motor into a reciprocating movement;
a vacuum generator connected to the power transmission unit to generate a vacuum pressure by introducing an external air or discharging the introduced air, wherein the vacuum generator comprises a valve connected to the power transmission member, a fixation member having a central opening portion for receiving the valve and a fixation plate, a valve seat positioned under the fixation member, and an air in-outputting member positioned under the valve seat to control the introduction and discharging of the air together with the valve seat by the operation of the valve, and wherein the valve seat comprises a hollowed portion for forming a vacuum space, inlet and outlet ports communicating with the vacuum space to introduce an air and discharge the introduced air, a plurality of subsidiary inlet ports radially surrounding the bottom side of the inlet port, and first and second switching plates selectively opening and closing the inlet and outlet ports according to the reciprocating movement of the valve;
a storage tank connected to the case from the outside such that the storage tank can be separated from the case, the storage tank air-communicating with the vacuum generator via an air-introducing tube;
an entrance tube externally combined with the storage tank to introduce a nasal mucus;
a guide tube attached to an inner wall of the storage tank to guide the introduced nasal mucus into the storage tank; and
a control unit for controlling the vacuum pressure in the vacuum generator to induce or stop the introduction of the nasal mucus.

17. The portable nasal mucus removing device of claim 16 wherein a circular groove surrounds the inlet and outlet ports, and an O-shaped ring is inserted into the groove to make the valve seat secret.

18. The portable nasal mucus removing device of claim 16 wherein the air in-outputting member comprises an inlet tube communicating with the inlet port to introduce an external air, an outlet tube communicating with the outlet port to discharge the introduced air to the outside, and a plurality of subsidiary outlet ports formed at the outlet tube while radially surrounding the bottom side of the outlet port.

19. The portable nasal mucus removing device of claim 16 wherein the first and second switching plates have a size capable of covering the inlet and outlet ports of the valve seat, but not the subsidiary inlet and outlet ports surrounding the inlet and outlet ports such that the first and second switching plates move upwards while opening the subsidiary inlet ports communicating with the inlet port and closing the outlet port to thereby introduce an external air, and the first and second switching plates move downwards while closing the inlet port and closing the outlet port communicating with the subsidiary outlet ports to thereby discharge the introduced air.

20. A portable nasal mucus removing device:
a case having an internal empty space for receiving parts;
a motor placed within the case and rotated by receipt of driving power from a battery;
a power transmission unit connected to the motor to convert the rotating movement of the motor into a reciprocating movement, wherein the power transmission unit comprises an eccentric cam fixed to a rotating shaft of the motor, a bearing surrounding the eccentric cam to minimize the rotational resistance of the motor and support the rotating shaft, and a power transmission member connected to the bearing to convert the rotating movement of the motor into a reciprocating movement;
a vacuum generator connected to the power transmission unit to generate a vacuum pressure by introducing an external air or discharging the introduced air, wherein the vacuum generator comprises a valve connected to the power transmission member, a fixation member having a central opening portion for receiving the valve and a fixation plate, a valve seat positioned under the fixation member, and an air in-outputting member positioned under the valve seat to control the introduction and discharging of the air together with the valve seat by the operation of the valve, wherein a protrusion is extended from the bottom side of the air in-outputting member, and the protrusion is provided with an extension tube for controlling the vacuum pressure in the vacuum generator;

a storage tank connected to the case from the outside such that the storage tank can be separated from the case, the storage tank air-communicating with the vacuum generator via an air-introducing tube;

an entrance tube externally combined with the storage tank to introduce a nasal mucus;

a guide tube attached to an inner wall of the storage tank to guide the introduced nasal mucus into the storage tank; and a control unit for controlling the vacuum pressure in the vacuum generator to induce or stop the introduction of the nasal mucus.

21. A portable nasal mucus removing device:

a case having an internal empty space for receiving parts;

a motor placed within the case and rotated by receipt of driving power from a battery;

a power transmission unit connected to the motor to convert the rotating movement of the motor into a reciprocating movement;

a vacuum generator connected to the power transmission unit to generate a vacuum pressure by introducing an external air or discharging the introduced air;

a storage tank connected to the case from the outside such that the storage tank can be separated from the case, the storage tank air-communicating with the vacuum generator via an air-introducing tube, wherein a blocking member is provided within the storage tank to prevent passage of the contents of the nasal mucus having viscosity but allow passage of a water content;

an entrance tube externally combined with the storage tank to introduce a nasal mucus;

a guide tube attached to an inner wall of the storage tank to guide the introduced nasal mucus into the storage tank; and a control unit for controlling the vacuum pressure in the vacuum generator to induce or stop the introduction of the nasal mucus.

\* \* \* \* \*